United States Patent
Wanunu et al.

(10) Patent No.: US 9,267,917 B2
(45) Date of Patent: Feb. 23, 2016

(54) NANOPORES IN ZERO MODE WAVEGUIDES

(71) Applicants: Northeastern University, Boston, MA (US); Pacific Biosciences of California, Inc., Menlo Park, CA (US)

(72) Inventors: Meni Wanunu, Chestnut Hill, MA (US); Jonas Korlach, Newark, CA (US); Mathieu Foquet, San Jose, CA (US); Stephen Turner, Menlo Park, CA (US)

(73) Assignee: Pacific Biosciences of California, Inc., Menlo Park, CA (US)

( * ) Notice: Subject to any disclaimer, the term of this patent is extended or adjusted under 35 U.S.C. 154(b) by 437 days.

(21) Appl. No.: 13/669,186

(22) Filed: Nov. 5, 2012

(65) Prior Publication Data
US 2013/0240356 A1    Sep. 19, 2013

Related U.S. Application Data

(60) Provisional application No. 61/555,835, filed on Nov. 4, 2011.

(51) Int. Cl.
| | |
|---|---|
| C12M 1/00 | (2006.01) |
| C12Q 1/68 | (2006.01) |
| C12M 1/34 | (2006.01) |
| C12M 3/00 | (2006.01) |
| G01N 15/06 | (2006.01) |
| G01N 33/00 | (2006.01) |
| G01N 33/48 | (2006.01) |
| G01N 21/64 | (2006.01) |
| G01N 21/00 | (2006.01) |
| G02B 6/10 | (2006.01) |
| C07H 21/02 | (2006.01) |
| G01N 27/447 | (2006.01) |

(Continued)

(52) U.S. Cl.
CPC ........ G01N 27/44791 (2013.01); G01N 27/447 (2013.01); G01N 33/48721 (2013.01); G02B 6/00 (2013.01)

(58) Field of Classification Search
USPC .............. 435/6.1, 283.1, 287.2, 288.4, 288.7; 536/23.1; 422/68.1, 82.07, 82.11; 385/129; 204/451
See application file for complete search history.

(56) References Cited

U.S. PATENT DOCUMENTS

| | | | |
|---|---|---|---|
| 5,547,839 A | 8/1996 | Dower et al. | |
| 6,210,896 B1 | 4/2001 | Chan | |

(Continued)

FOREIGN PATENT DOCUMENTS

WO    9905315 A2    2/1999

OTHER PUBLICATIONS

Miyake et al, Real-Time Imaging of Single-Molecule Fluorescence with a Zero-Mode Waveguide for the Analysis of Protein-Protein Interaction, 2008, 80, 6018-6022.*

(Continued)

Primary Examiner — Narayan Bhat
(74) Attorney, Agent, or Firm — Robert H. Reamey

(57) ABSTRACT

Methods, devices, substrates, and systems are disclosed involving arrays of zero-mode waveguides having nanopores extending through the bases that form the bottoms of the zero-mode-waveguides. Electric fields across the nanopores are used to attach single biomolecules such as polymerase enzymes within each zero-mode-waveguide. Electric fields across the nanopores can also be used for the active loading of nucleic acid templates into enzymes attached within the zero mode waveguides.

18 Claims, 8 Drawing Sheets

(51) Int. Cl.
*G02B 6/00* (2006.01)
*G01N 33/487* (2006.01)

(56) References Cited

U.S. PATENT DOCUMENTS

| | | |
|---|---|---|
| 6,255,083 B1 | 7/2001 | Williams |
| 6,787,308 B2 | 9/2004 | Balasubramanian et al. |
| 6,917,726 B2 | 7/2005 | Levene et al. |
| 7,013,054 B2 | 3/2006 | Levene et al. |
| 7,056,661 B2 | 6/2006 | Korlach et al. |
| 7,170,050 B2 | 1/2007 | Turner et al. |
| 7,486,865 B2 | 2/2009 | Foquet et al. |
| 7,692,783 B2 | 4/2010 | Lundquist et al. |
| 7,714,303 B2 | 5/2010 | Lundquist et al. |
| 7,805,081 B2 | 9/2010 | Lundquist et al. |
| 7,907,800 B2 | 3/2011 | Foquet et al. |
| 7,935,310 B2 | 5/2011 | Korlach |
| 8,137,942 B2 | 3/2012 | Roitman et al. |
| 8,193,123 B2 | 6/2012 | Rank et al. |
| 2003/0096253 A1 | 5/2003 | Nelson |
| 2003/0190647 A1 | 10/2003 | Odera |
| 2003/0215862 A1 | 11/2003 | Parce et al. |
| 2004/0048300 A1 | 3/2004 | Sood et al. |
| 2004/0152119 A1 | 8/2004 | Sood et al. |
| 2004/0224319 A1 | 11/2004 | Sood et al. |
| 2007/0172386 A1* | 7/2007 | Li et al. ............... 422/58 |
| 2008/0080059 A1 | 4/2008 | Dixon et al. |
| 2009/0118129 A1 | 5/2009 | Turner |
| 2010/0065726 A1* | 3/2010 | Zhong et al. ............. 250/227.24 |
| 2010/0099100 A1 | 4/2010 | Zaccarin et al. |
| 2011/0117637 A1 | 5/2011 | Gray et al. |
| 2011/0222179 A1 | 9/2011 | Monadgemi |
| 2011/0256618 A1 | 10/2011 | Eid et al. |
| 2011/0257040 A1 | 10/2011 | Turner et al. |
| 2011/0278475 A1 | 11/2011 | Lundquist et al. |

OTHER PUBLICATIONS

Miyake et al, Supplementary information Figure 1, p. 1, printed on Feb. 26, 2015.*
Miyake et al, Supplementary information Figure 2, p. 1, printed on Feb. 26, 2015.*
Larkin et al, Reversible Positioning of Single Molecules inside Zero-Mode Waveguides, 2014, Nano Lett., 14, 6023-6029.*
Larkin et al, Reversible Positioning of Single Molecules inside Zero-Mode Waveguides, 2014, Nano Lett., 14, 6023-6029, Supplemental information, pp. 1-10.*
Eid et al., "Real-Time DNA Sequencing From Single Polymerase Molecules," Science (2009) 323:133-138.
Hong et al., "Self-Assembly of a Dendron Through Multiple Ionic Interaction to Give Mesospacing Between Reactive Amine Groupe on the Surface," Langmuir (2003) 19:2357-2365.
Levene et al., "Zero-mode Waveguides for Single-molecule Analysis at High Concentration" Science (2003) 299:682-686.

* cited by examiner

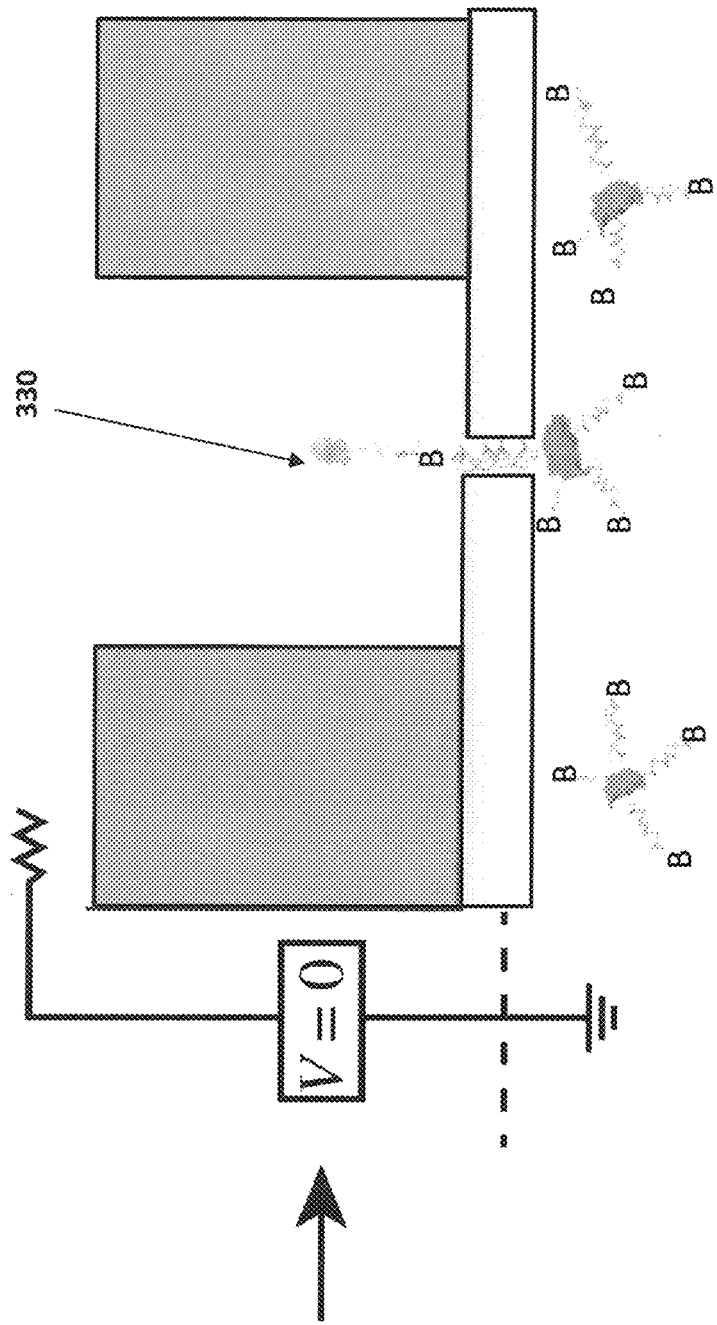

SEQUENCE LISTING

<160> NUMBER OF SEQ ID NOS: 4

<210> SEQ ID NO 1
<211> LENGTH: 11
<212> TYPE: DNA
<213> ORGANISM: Artificial Sequence
<220> FEATURE:
<223> OTHER INFORMATION: synthesized

<400> SEQUENCE: 1
tcttgatgta c                                                                11

<210> SEQ ID NO 2
<211> LENGTH: 11
<212> TYPE: DNA
<213> ORGANISM: Unknown
<220> FEATURE:
<223> OTHER INFORMATION: bacterial
<220> FEATURE:
<221> NAME/KEY: modified_base
<222> LOCATION: (7)..(7)
<223> OTHER INFORMATION: m6a
<220> FEATURE:
<221> NAME/KEY: misc_feature
<222> LOCATION: (7)..(7)
<223> OTHER INFORMATION: n is a, c, g, or t

```
<400> SEQUENCE: 2
tacttgntcg a                                                          11

<210> SEQ ID NO 3
<211> LENGTH: 11
<212> TYPE: DNA
<213> ORGANISM: Unknown
<220> FEATURE:
<223> OTHER INFORMATION: bacterial

<400> SEQUENCE: 3
tacttgatcg a                                                          11

<210> SEQ ID NO 4
<211> LENGTH: 15
<212> TYPE: DNA
<213> ORGANISM: Unknown
<220> FEATURE:
<223> OTHER INFORMATION: bacterial

<400> SEQUENCE: 4
gctcgatcaa gtaca                                                      15
```

NANOPORES IN ZERO MODE WAVEGUIDES

CROSS-REFERENCE TO RELATED APPLICATIONS

This application claims priority to U.S. Provisional Application No. 61/555,835 filed Nov. 4, 2011, the entire contents of which are incorporated herein for all purposes by this reference.

STATEMENT REGARDING FEDERALLY SPONSORED RESEARCH

Not Applicable.

INCORPORATION-BY-REFERENCE OF MATERIAL SUBMITTED BY U.S.P.T.O. eFS-WEB

The instant application contains a Sequence Listing which is being submitted in computer readable form via the United States Patent and Trademark Office eFS-WEB system, and is hereby incorporated by reference in its entirety for all purposes. The txt file submitted on Jun. 23, 2015 contains only 2 KB file 07-000101_2015-06-23_2ndAmendedSequenceListing.

BACKGROUND OF THE INVENTION

Since the complete sequencing of the human genome by the U.S. Department of Energy and the NIH in 2003, extensive research has been focused on understanding human genetics and how it impacts our health. The ability to sequence complete genomes and the vast amount of existing sequence data has led to widespread advancements in all areas of health care, from preventative treatment to early detection to optimization in therapy. Knowledge of an individual's genotype can maximize the probability of successful treatment by reducing trial-and-error prescribing, increasing patient compliance with therapy, and reducing adverse drug reactions. Today, genetic testing plays a role in the surveillance and treatment of a number of disorders, including various types of cancer, coagulation disorders, and cardiac health. Personalized genomics can also revolutionize medicine by improving the selection of targets for drug discovery, reducing the time, cost, and failure rate of clinical trials, and avoiding the withdrawal of marketed drugs. In addition to DNA sequence, knowledge of an individual's epigenetic makeup and DNA damage profile can assist in the diagnosis and treatment of disease, and has been implicated in important biological processes such as aging and neurological diseases such as Alzheimer's and Parkinson's disease.

Despite progress, the new era of personalized health for every individual is impeded by the high costs of genome sequencing and DNA analysis. Without large reductions in sequencing costs, genome sequencing cannot be used routinely for individual health care. This need to reduce cost while maintaining sequencing quality has sparked the $1100 genome program by the NHGRI, which has catalyzed many innovative approaches to DNA sequencing (see e.g. Schloss et al. Nature Biotechnology 2008, 26 (10), 1113-1115). The current invention provides for improved sequencing.

BRIEF SUMMARY OF THE INVENTION

In some aspects the invention provides an array of zero mode waveguides, each zero mode waveguide comprising an aperture having walls and a base, and each zero mode waveguide having a nanopore extending through its base.

In some embodiments each aperture extends through an opaque cladding layer to a base layer, the base layer comprising the base of the aperture. In some embodiments the opaque cladding layer comprises a metal. In some embodiments the opaque cladding layer comprises aluminum. In some embodiments the base layer comprises silicon nitride. In some embodiments the apertures have a cross sectional dimension of between about 20 nm and 300 nm. In some embodiments the nanopores have a cross sectional dimension between about 2 nm and 10 mm.

In some embodiments the array comprises a silicon substrate. In some embodiments the opaque cladding layer and the base layer are each coated with a passivating layer. In some embodiments the passivating layer comprises polyethylene glycol.

In some aspects the invention provides a method for isolating a single biomolecule within a zero mode waveguide comprising: providing an array of zero mode waveguides on a substrate, each zero mode waveguide having a base layer comprising its base, each zero mode waveguide having a nanopore through its base; exposing the bottom of the zero mode waveguide to a solution comprising attachment molecules, the attachment molecules having a threading portion which can extend through the nanopore, and a blocking portion which does not pass through the pore, wherein the threading portion comprises a binding moiety; providing an electric field across the array that drives the threading portion of the attachment molecules into the nanopores; adding biomolecules to the top of the array comprising a group capable of reaction with the binding moiety; allowing the biomolecules to react with the binding moieties whereby a single biomolecule is isolated within a plurality of the zero mode waveguides.

In some embodiments the blocking portions of the attachment molecules comprise a protein, a bead, or a nanoparticle. In some embodiments the attachment molecule comprises avidin or streptavidin. In some embodiments threading portion of the attachment molecules comprise a nucleic acid. In some embodiments the nucleic acid comprises DNA. In some embodiments the binding moiety on the threading portion comprises biotin.

In some embodiments the group on the biomolecule capable of reacting with the binding moiety comprises avidin or streptavidin. In some embodiments the biomolecule comprises a polymerase enzyme.

In some aspects the invention provides a method for isolating single polymerase enzymes within a zero mode waveguides comprising: providing an array of zero mode waveguides on a substrate, each zero mode waveguide having a nanopore through its base; exposing the bottom of the zero mode waveguide to a solution comprising attachment molecules, the attachment molecules having a threading portion which can extend through the nanopore, and a blocking portion which does not pass through the pore, wherein the threading portion comprises an binding moiety; providing an electric field across the array that drives the threading portion of the attachment molecules into the nanopores; adding polymerase enzymes, each comprising a group capable of reaction with the binding moiety to the top of the array; and allowing the polymerase enzymes to react with the binding moieties whereby a single biomolecule is isolated in a plurality of the zero mode waveguides.

In some aspects the invention further comprises adding nucleic acid templates to the top of the array and providing an electric field across the array to drive the nucleic acid templates into the zero mode waveguides.

In some embodiments a salt gradient is formed in order to enhance driving of the biomolecules into the zero mode waveguides.

In some aspects the invention provides a method of actively loading nucleic acid templates into an array of zero mode waveguides comprising: providing an array of zero mode waveguides on a substrate, each zero mode waveguide having a nanopore through its base, wherein a plurality of the zero mode waveguides have a single polymerase enzyme attached within them; adding nucleic acid templates to the top of the array and providing an electric field across the array to drive the nucleic acid templates into the zero mode waveguides whereby at least some of the templates become complexed by the polymerase enzymes in the zero mode waveguides.

In some embodiments a salt gradient is formed in order to enhance driving of the nucleic acids into the zero mode waveguides.

In some embodiments the nucleic acid templates are primed.

In some aspects the invention provides a method of nucleic acid sequencing comprising: providing an array of zero mode waveguides on a substrate, each zero mode waveguide having a nanopore though its base, each nanopore having an attachment molecule with a blocking portion below the nanopore, and a threading portion extending into the nanopore, the threading portion bound to a single polymerase enzyme, the enzyme complexed with a template nucleic acid; contacting the tops of the zero mode waveguides with a solution having the reagents necessary for nucleic acid sequencing including a plurality of phosphate labeled nucleotide analogs, each with a different fluorescent label, carrying out enzyme mediated nucleic acid synthesis to produce a growing strand from the nucleotide analogs complementary to the template nucleic acid; illuminating the array of zero mode waveguides from below with excitation light, observing the fluorescent signals of the nucleotide analogs while they are being incorporated into the growing chain, and prior to cleavage and release of the label to obtain a time sequence of fluorescent signals; and using the time sequence of fluorescent signals to determine a sequence of the template nucleic acid.

In some embodiments the attachment molecule comprises a protein blocking portion and a nucleic acid threading portion.

BRIEF DESCRIPTION OF THE DRAWINGS

FIG. 3 shows a ZMW-nanopore devices employed for high yield loading of one DNA polymerase per ZMW. In FIG. 3(C) excess DNA polymerase is washed away.

DETAILED DESCRIPTION OF THE INVENTION

Figure 1A:
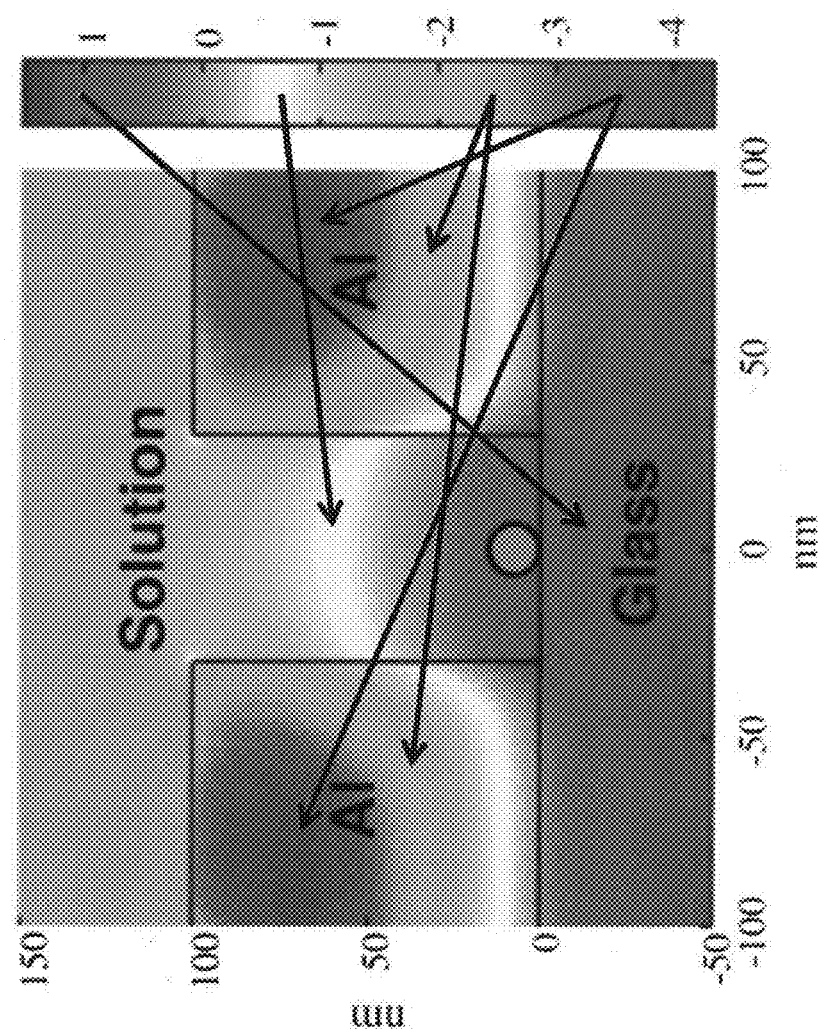
FIG. 1(A) shows a three-dimensional finite-element simulation of the light intensity distribution

The invention is directed to improved devices, methods, substrates, and systems for nucleic acid sequencing, and in particular, single molecule real time nucleic acid sequencing. In some aspects, the invention provides for controlling the position and number of polymerase molecules within a ZMW, which improves the yield and sensitivity of single molecule real time nucleic acid sequencing. The arrays and methods of the invention provide for limiting the number of active nucleic acid polymerases in each ZMW to exactly one. Since nucleic acid sequence information is obtained by translating the observed temporal dynamics of nucleotide incorporation, having more than one polymerase in the same ZMW results in signals that are difficult to interpret. In some preparation schemes that have been described, the ZMW's bottom surface is selectively functionalized with biotin groups, and then an avidin-polymerase/DNA template complex is added to the bulk to react with the surface (see e.g. Korlach et al. Nucleosides Nucleotides Nucleic Acids 2008, 27 (9), 1072-1083). This process results in some ZMWs with a mixed number of polymerase molecules, with the theoretical limit of usable ZMWs being about 37%, which reduces the sequencing throughput and increases cost.

There is also a need for sequencing small amounts of nucleic acids (e.g. picogram levels of DNA) without amplification. Because single molecule real time technology is based on sequencing individual nucleic acid molecules, a slow step for sequencing initiation is the process of polymerase enzyme and template (e.g. DNA) loading into the ZMW glass bottom, typically dictated by free diffusion of DNA/polymerase complexes towards the ZMW. This reliance on diffusion can be problematic for analysis of samples of limited availability, for example, epigenetic analysis of DNA extracted from living brain tissue that cannot be amplified. The invention provides for efficient and reproducible fabrication of ZMW-nanopore devices, efficient DNA sequencing, and on enhancing input DNA loading rates into the ZMW for direct sequencing from picogram levels of human brain mitochondrial DNA.

We have invented a novel approach to this issue that involves replacing the glass bottom of each ZMW in an array with an ultrathin membrane that contains a nanopore. Our novel approach offers several advantages: First, it allows a high yield of single DNA polymerase loading in a precise position with respect to each ZMW. Second, it permits the use of ion gradients across the nanopore for enhancing the loading rate of DNA molecules into the ZMW for sequencing. Third, it allows reversible anchoring/de-anchoring of the polymerase from the ZMW by applying an electrical voltage that can be used to dispose of faulty polymerases and introduce fresh polymerases into ZMWs. These combined advantages can dramatically reduce the cost of DNA sequencing, and in addition enable a unique platform for sequencing and analyzing native DNA samples at picogram levels while preserving epigenetic information.

Figure 1B:
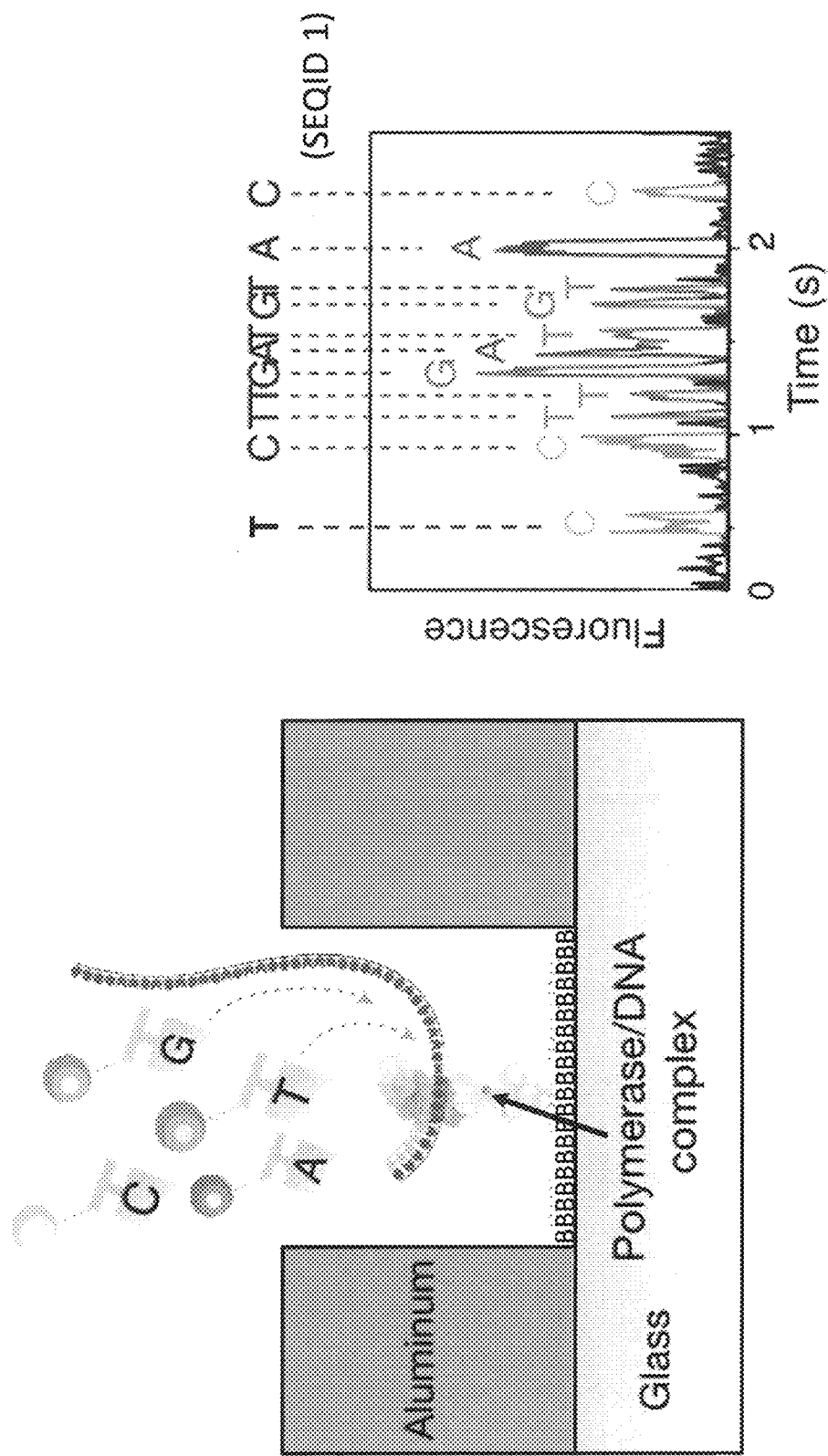
FIG. 1(B) shows how a single DNA polymerase can be immobilized inside the ZMW using biotin/streptavidin chemistry and time-resolved 4-color fluorescence can be used to report the sequence.

FIG. 1 shows a Zero-mode waveguide (ZMW) platform for single-molecule, real-time DNA sequencing. FIG. 1(A) shows a three-dimensional finite-element simulation of the light intensity distribution (log scale) for a ZMW 50 nm in diameter and 100 nm in height (see Levene et al. Science 2003, 299 (5607), 682-686 for a color version of the figure, incorporated in its entirety herein by reference. The dot at the base of the ZMW represents an ideal position of a polymerase for SMRT DNA sequencing. As illustrated in FIG. 1(B), in a functional ZMW, a single DNA polymerase can be immobilized inside the ZMW using biotin/streptavidin chemistry and time-resolved 4-color fluorescence reports the sequence (see Eid et al. Science 2009, 323 (5910), 133-138, and U.S. Pat. No. 7,056,661 (Korlach et al.) which are incorporated in their entirety herein by reference). Reaction of the multi-biotinylated surface with streptavidin/polymerase complexes results in less than 37% yield of functional ZMWs with one polymerase in a ZMW, whereas the majority of the ZMWs are defective because often there are either too many or no polymerases in the ZMWs.

Of the many approaches for genome sequencing, multiplexed single-molecule techniques offer invaluable potential advantages over bulk methods such as reduced cost of reagents, increased read lengths, and improved accuracy by multiple reads, see Branton et al., Nature Biotechnology 2008, 26 (10), 1146-1153 and Schadt et al., Hum. Mo. Genet. 2010, 19, R227-R240 incorporated in their entirety herein by reference. Commercial instruments for carrying out such sequencing have been introduced by Pacific Biosciences of California, Inc., which is designing, developing, and commercializing technologies for genomic and epigenomic DNA sequencing at the single-molecule level, see Flusberg, et al. Nature Methods 2010, 7 (6), 461-465 and Korlach et al. Nucleosides Nucleotides Nucleic Acids 2008, 27 (9), 1072-1083 incorporated in their entirety herein by reference.

The single-molecule real-time technology identifies the sequence of nucleotides incorporated by a single DNA polymerase using 4-color fluorescence microscopy. A key technology that enables this fluorescence-based analysis is the zero-mode waveguide (ZMW) array, an array of holes with sub-wavelength dimensions fabricated in an opaque metallic mirror film (see FIG. 1). Dye-labeled terminal phosphate-linked nucleotides (see e.g. Sood, A et al. J. Am. Chem. Soc. 2005, 127 (8), 2394-2395 incorporated in its entirety herein by reference) in the solution above the ZMWs are used to signal base incorporation by the polymerase in real time, observed as distinct bursts of fluorescence. The ZMW confines light excitation to the region of the polymerase, enabling high bulk concentrations of fluorescent nucleotides to be used for high-throughput sequencing with minimal background fluorescence. In recent years, SMRT sequencing has been applied for high-quality genome sequencing, see Chin et al. N. Engl. J. Med. 2011, 365 (8), 709-717 incorporated in its entirety herein by reference. SMRT technology also has the ability to detect modified bases during sequencing, which is both important and unique for progress in epigenomic analysis.

Fabrication of ZMWs on glass substrates has been demonstrated, see Foquet et al. J. Appl. Phys. 2008, 103 (3), 034301 incorporated in its entirety herein by reference. Fabrication of nanopores in thin membranes has also been shown, see Kim et al., Adv. Mater. 2006, 18 (23), 3149 and Wanunu, M. et al., Nature Nanotechnology 2010, 5 (11), 807-814 incorporated in their entirety herein by reference. The fabrication of ZMW-nanopore devices can be accomplished through the integration of these two processes in a manner that has not been contemplated heretofore. Zero Mode Waveguides are described, for example in U.S. Pat. No. 6,917,726 Zero-Mode Metal Clad Waveguides for Performing Spectroscopy with Confined Effective Observation Volumes; U.S. Pat. No. 7,013,054 Zero-Mode Metal Clad Waveguides for Performing Spectroscopy with Confined Effective Observation Volumes; U.S. Pat. No. 7,170,050 Arrays of optical confinements and uses thereof; U.S. Pat. No. 7,486,865 Substrates for performing analytical reactions; U.S. Pat. No. 7,907,800 Methods for monitoring reactions in zero mode waveguides; US 20110222179 Micromirror Arrays Having Self Aligned Features; US 20110117637 Zero-Mode Waveguides with Non-Reflecting Walls; US 20100099100 Ultra-High Multiplex Analytical Systems and Methods; and US 20110257040 Nanoscale Apertures Having Islands of Functionality which are incorporated herein by reference in their entirety for all purposes.

Figure 2:
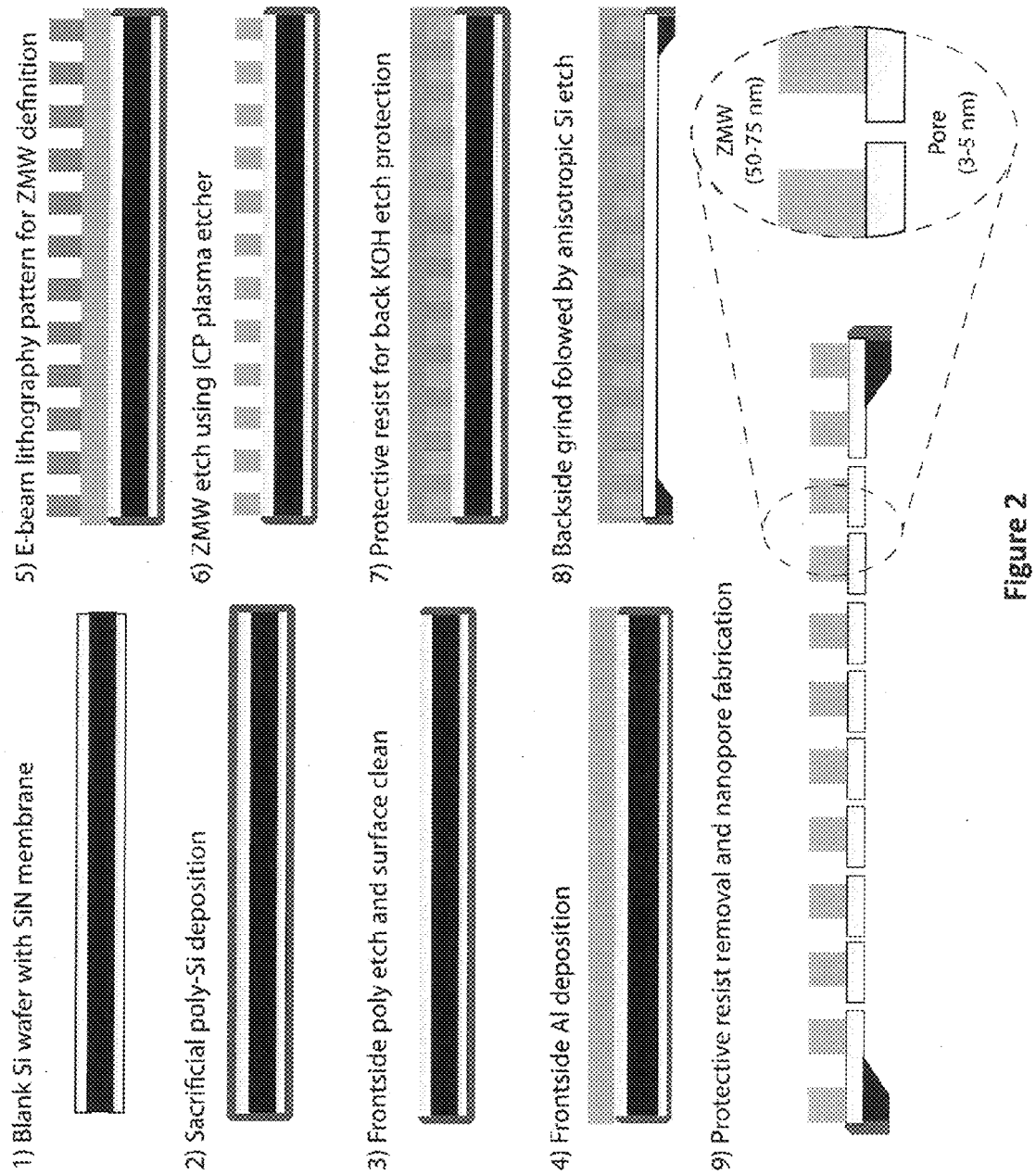
FIG. 2 shows an exemplary process of the invention for producing ZMW-nanopore arrays.

An exemplary process is outlined in FIG. 2, and begins, for example, with a 4" diameter, 170 μm thick Si wafer that contains an ultrathin (~20 nm) silicon nitride (SiN) membrane on its front and back sides. The thickness of the ultrathin membrane can be from about 3 nm to about 50 nm, or about 5 nm to about 30 nm. Generally the thickness across the wafer varies such that there are thicker regions to provide mechanical stability, and thin regions comprising the SiN membrane near the zero mode waveguides to allow for the nanopore to have the appropriate dimensions. In some cases there is a thin portion of the wafer for each ZMW, in some cases, the thin portion of the wafer extends across multiple ZMW's, for example extending across 10 to 10,000 ZMWs, or across 10 to 100 ZMWs. The Si wafer is modified through a series of steps to form an aluminum-based ZMW array on the SiN membrane (See, for example, FIG. 2, Steps 1-7). In some cases, the methods of the invention include the use of both a Si wafer and a SiN membrane.

In Step 8 of the process, the Si wafer is anisotropically etched to produce freestanding transparent SiN windows. Following removal of the protective resist, the optically transparent SiN membranes permit trans-membrane fluorescence imaging of single molecules. The ZMW-processed Si wafer is then cut into individual dyes, e.g. from a 4" wafer into 200 5 mm×5 mm dies. The final step is the fabrication of single nanopores at the center of each ZMW using a field-emission transmission electron microscope (FE-TEM). Centering of the pores in the ZMWs can be achieved by manual or automatic translation of the electron beam. The arrays can have for example, about 10, 100, 1000, 10,000, a million, or more than a million ZMW-nanopores. They can have, for example, between 10 and 1000, between 10 and 10,000, or between 1,000 and 100,000 or between 1,000 and a million ZMW-pores. The nanopores can be formed by any suitable method. For example, they can be formed using electron beams, He-ions, or focused ion beam drilling. The size of the nanopores can be from about 1 nm to about 20 nm or from about 2 nm to about 10 mm, or from about 3 nm to about 5 nm. The ZMW typically has a circular profile having a diameter from about 40 nm to about 300 nm, or from about 50 nm to about 200 nm. The ZMW can have any suitable profile including elliptical or rectangular, having at least one dimension from 40 nm to about 300 nm, or from about 50 nm to about 200 nm Manufactured ZMW-nanopore samples can be examined to determine the yield of functional devices. The morphology of the ZMWs can be characterized through scanning electron microscopy to assess the ZMW size, atomic force microscopy to characterize the ZMW profile, transmitted light analysis to quantify optical leakage through the waveguide, and cross-sectional TEM to characterize the side walls of the ZMW. For the nanoscale ZMW-nanopore hybrids of the invention, surface properties are typically controlled for optimal performance. For example, hydration of synthetic pores with electrolyte solution can be obtained with proper process control and surface treatment. For example, Wanunu, has recently found that thinning SiN membranes results in nearly 100% pore wetting yield. Treatment strategies include chemical modification (Wanunu et al. Nano Lett. 2007, 7 (6), 1580-1585 incorporated in its entirety herein by reference) and atomic layer deposition (Merchant et al., Nanopores. Nano Lett. 2010, 10 (8), 2915-2921 incorporated in its entirety herein by reference. Passivation of the surfaces of the ZMW is typically done to improve performance and prevent non-specific absorption, for example, selective passivation of Al surfaces for mitigating non-specific biomolecular adsorption is described in Korlach, J. et al. Nucleosides Nucleotides Nucleic Acids 2008, 27 (9), 1072-1083 incorporated in its entirety herein by reference. Obtaining the proper wetting behaviour and using testing to determine its effectiveness is well known in the art. Exemplary techniques to improve wetting are oxygen plasma treatment and treatment with piranha solution. Selective surface treatment for use in the instant invention is described, for example, in U.S. Pat. No. 5,624,711; U.S. Pat. No. 5,919,523; Hong et al., (2003) Langmuir 2357-2365; U.S. Pat. No. 5,143,854; U.S. Pat. No. 5,424,186; U.S. Pat. No. 7,763,423 Reactive surfaces, substrates and methods of producing and using same; U.S. Pat. No. 8,137,942 Reactive surfaces, substrates and methods of producing and using same; U.S. Pat. No. 7,993,891 Reactive surfaces, substrates and methods of producing and using same; U.S. Pat. No. 7,935,310 Uniform surfaces for hybrid material substrates and methods of making and using same; U.S. Pat. No. 7,932,035 Uniform surfaces for hybrid material substrates and methods of making and using same; U.S. Pat. No. 7,931,867 Uniform surfaces for hybrid material substrates and methods of making and using same; and U.S. Pat. No. 8,193,123 Articles having localized molecules disposed thereon and methods of producing same which are incorporated herein by reference in their entirety for all purposes.

One aspect of the invention is the insertion of individual binding groups, e.g. biotin moities, into nanopores for subsequent immobilization of individual DNA polymerases. This can be accomplished using attachment molecules having a threading portion which can extend through the nanopore, and a blocking portion which does not pass through the pore, where the threading portion has a single binding moiety loading the single binding moiety, e.g. biotin into pores (see FIG. 3(A), Step A). One approach uses a double stranded DNA as the threading portion. For example an attachment molecule can be produced starting with a 50-75 bp double-stranded DNA (dsDNA) molecule with biotin on both ends. The DNA is prepared by annealing two synthetic self-complementary oligos that each contain a biotin group at the 5'-end. The dsDNA molecule is reacted with avidin in a large DNA excess to saturate the biotin binding sites, generating an avidin-dsDNA-biotin (ADB) construct that acts as an attachment molecule (see FIG. 3).

Figure 3A:
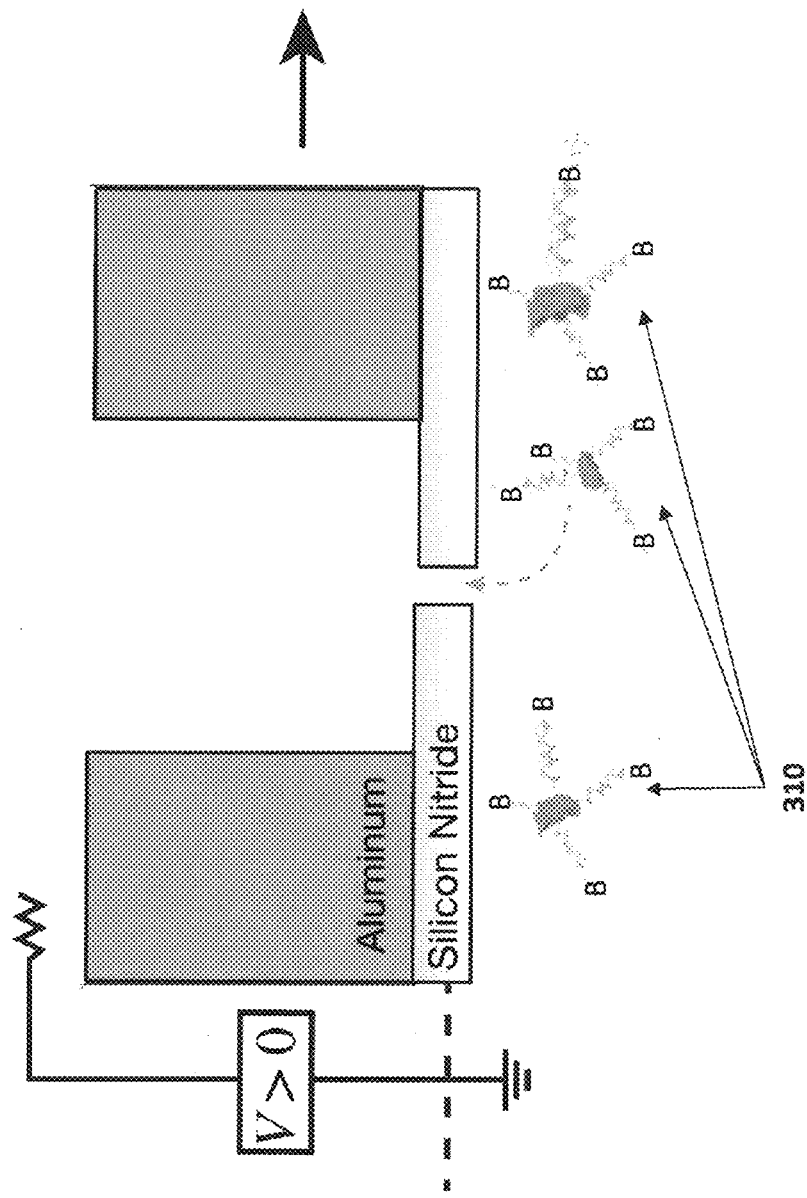
In FIG. 3(A) voltage is applied to anchor an attachment molecule such as a bulky avidin-DNA-biotin molecule into a pore.
Figure 3B:
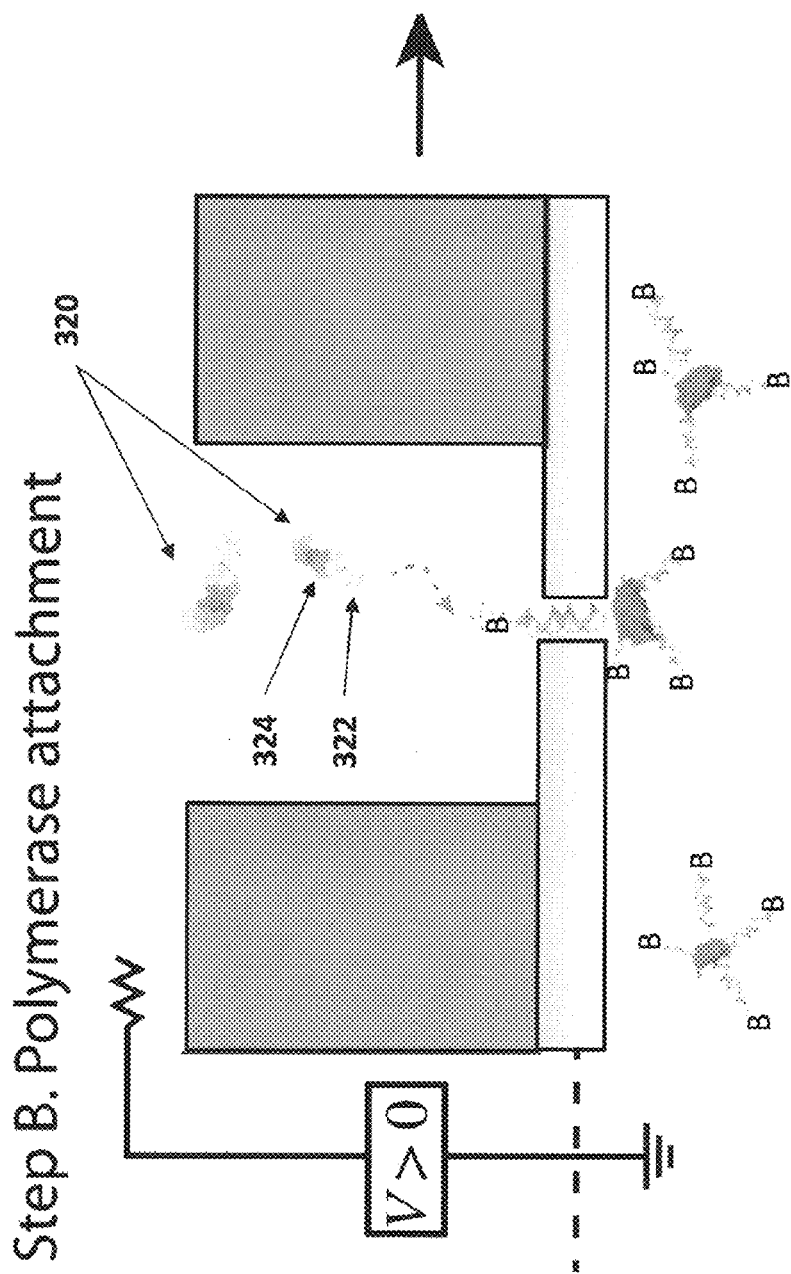
In FIG. 3(B) a DNA polymerase having an avidin or streptavidin portion is allowed to react with the solitary biotin group in each ZMW.

FIG. 3 shows a ZMW-nanopore devices employed for obtaining high loading of one DNA polymerase per ZMW. In Step A, FIG. 3(A), voltage is applied to anchor an attachment molecule such as a bulky avidin-DNA-biotin molecule (ADB) 310 into a pore. The biotin groups are designated by the letter B. Because of the pore size, DNA preferentially threads into the pore, exposing a biotin group for reaction with a streptavidin-polymerase complex in the top chamber. In Step B, FIG. 3(B), a DNA polymerase with a binding portion 320 comprising, for example, a DNA polymerase 324 having an avidin or streptavidin portion 322, is allowed to react with the solitary biotin group in each ZMW, obtaining single polymerase loading, a prerequisite for single molecule real time DNA sequencing. The potential loading efficiency for 1:1 ZMW:polymerase is 100%, vs. the current Poissonian limit of ~37%. In Step C, FIG. 3(C), excess DNA polymerase is washed away, after which DNA can be introduced into the top chamber for complexation with the immobilized polymerase and sequencing. Here, the polymerase is attached, then template DNA is introduced. In other cases, a polymerase-nucleic acid complex is introduced in step B resulting in the direct connection of the nucleic acid-polymerase complex, obviating the need for a subsequent addition of template nucleic acid. The SiN membrane can be coated with a PEG-silane in order to reduce non-specific polymerase binding. Exemplary treatments for reducing non-specific binding include self-assembled monolayers of PEG, and atomic-layer deposition of oxides or nitrides.

In some embodiments of the invention, the threading portion (e.g. double stranded DNA) is attached to the nucleic acid polymerase or the polymerase-template complex. The threaded polymerase is then introduced from above such that the threading portion is passed into the nanopore. On the opposite side of the nanopore is an attachment molecule (e.g. avidin or streptavidin) that will react with a group that threads through the pore (e.g. biotin), blocking the threading portion from coming back out of the nanopore. In this way, each single polymerase or complex blocks the threading of a second entity, providing for single loading.

The attachment molecule can be made with any suitable combination of threading portions and blocking portions. In some cases, the blocking portions are proteins. In other cases, the blocking portions can be other bulky groups such as beads or nanoparticles. The blocking portions, e.g. beads and nanoparticles can have sizes, for example of about 5 nm to 500 nm, from about 10 nm to about 200 nm or from about 10 nm to about 40 nm. The size of the blocking group is related to the size of the nanopore. The relative sizes of these can be adjusted in order to improve performance and manufacturability.

The thickness of the base layer such as silicon nitride can be adjusted to optimize performance, to aid in processing, and to minimize autofluorescence. The thickness of the base layer such as silicon nitride is generally about 3 nm to about 50 nm, or about 5 nm to about 30 nm, about 2 nm and about 30 nm in thickness or about 4 nm and about 15 nm in thickness.

In some embodiments, nanopore arrays in SiN membranes (without ZMWs) are assembled in a two-chamber electrolyte apparatus, and voltage is applied across the SiN membrane using a pair of electrodes (FIG. 3). Applied voltage generates a localized electric field near the pore, and has previously been used for immobilizing and interrogating DNA inside protein channels, see Sauer-Budge, A. F. et al, Biophys. J. 2004, 87 (5), 3205-3212; Cockroft, S. L et al, J. Am. Chem. Soc. 2008, 130 (3), 818; and Wanunu, M. et al. Phys. Rev, E 2008, 77 (3), 031904 incorporated in their entirety herein by reference, and solid-state nanopores, see McNally, B. et al. Nano Lett. 2008, 8 (10), 3418-3422; and Tabard-Cossa, V. et al., ACS Nano 2009, 3 (10), 3009-3014, incorporated in its entirety herein by reference. Based on the pore dimensions, only one DNA arm of the ADB construct threads into the pore, resulting in a single biotin site exposed on the top chamber. Varying the ADB molecule concentrations and applied voltage allows for control over the biotin-loading kinetics. In some cases, dendrimeric attachment molecules such as low-generation biotin dendrimers, see Wilbur, D. S. et al. Bioconjugate Chem. 1998, 9 (6), 813-825 incorporated in its entirety herein by reference, can be used to enhance loading kinetics by increasing the number of tether portions.

After completion of Step A, FIG. 3(A), for example, the process descried as above is carried out in the presence of a DNA polymerase-avidin containing solution in the top chamber (Step B, FIG. 3(B)). The exposed binding moiety such as biotin binds to the polymerase, e.g. DNA polymerase-avidin complex to create a locked complex that cannot readily exit the pore, thus anchoring the polymerase in the pore. After washing excess polymerase in Step C, FIG. 3(C), the array is loaded with polymerase and is in the condition for template DNA addition and subsequent polymerization. The stability of the complex can be readily determined by applying various voltages and measuring current.

After preparation of the polymerase-loaded ZMW-nanopore devices, DNA replication inside the ZMW-nanopore device can be carried out and followed using fluorescence microscopy. Sequencing using single-molecule real-time DNA sequencing as described above incorporating dye-labeled terminal phosphate-linked nucleotides to the template DNA can be carried out. The dye-terminated nucleotides are readily available. Stable binding of dye-labeled terminal phosphate-linked (phospholinked) nucleotides in the presence of non-catalytic divalent metal ions, such as $Ca^{2+}$, as well as DNA synthesis in the presence of catalytic metal ions, such as $Mg^{2+}$, can be monitored by replacing one of the four deoxynucleotide triphosphates (NTPs) used for DNA replication with a labeled nucleotide. The functionality of each polymerase in a ZMW-nanopore array can be assessed using a fluorescence microscope attached to a fast electron-multiplying CCD camera.

An additional aspect of the invention involves enhancing the rate of DNA template loading into ZMW-nanopores. The sensitivity of nanopores to picogram levels of long DNA fragments has recently been shown, see Wanunu, M. et al., Nature Nanotechnology 2010, 5 (2), 160-165 incorporated in its entirety herein by reference. By applying a salt gradient and voltage across a pore, DNA migrates from solution towards the pore, resulting in orders of magnitude improvement in DNA loading in the ZMWs (see FIG. 4). This method allows for the rapid loading of templates and for the loading of small amounts nucleic acids, for example, for loading picogram levels of DNA into ZMWs for complexation with the DNA polymerase. The rate of nucleic acid template loading can be adjusted by varying the ion gradients and voltages across the pore. Rates of loading can be determined using fluorescence microscopy. In some cases, using low voltage ramp slopes are used to prevent polymerase ejection from the pore. In some cases, the salt level is maintained in the top chamber to preserve polymerase activity, e.g. maintaining <50 mM KCl in the top chamber to preserve polymerase activity. The efficiency of the loading can be quantified using fluorescence-based assays. In some cases, the efficiency of DNA loading depends on the magnitude of the electric field outside the pore, which is related to the ion flux through the pore. These fields remain significant even when the DNA-polymerase complex is in the pore, because ion current is not completely blocked. Our approach differs from nanopore-based sequencing in that there is no need to electrically address each nanopore, see Branton, D et al., Nature Biotechnology 2008, 26 (10), 1146-1153 incorporated in its entirety herein by reference, since the applied voltage pulse loads DNA into all ZMW/nanopores in parallel.

Figure 4:
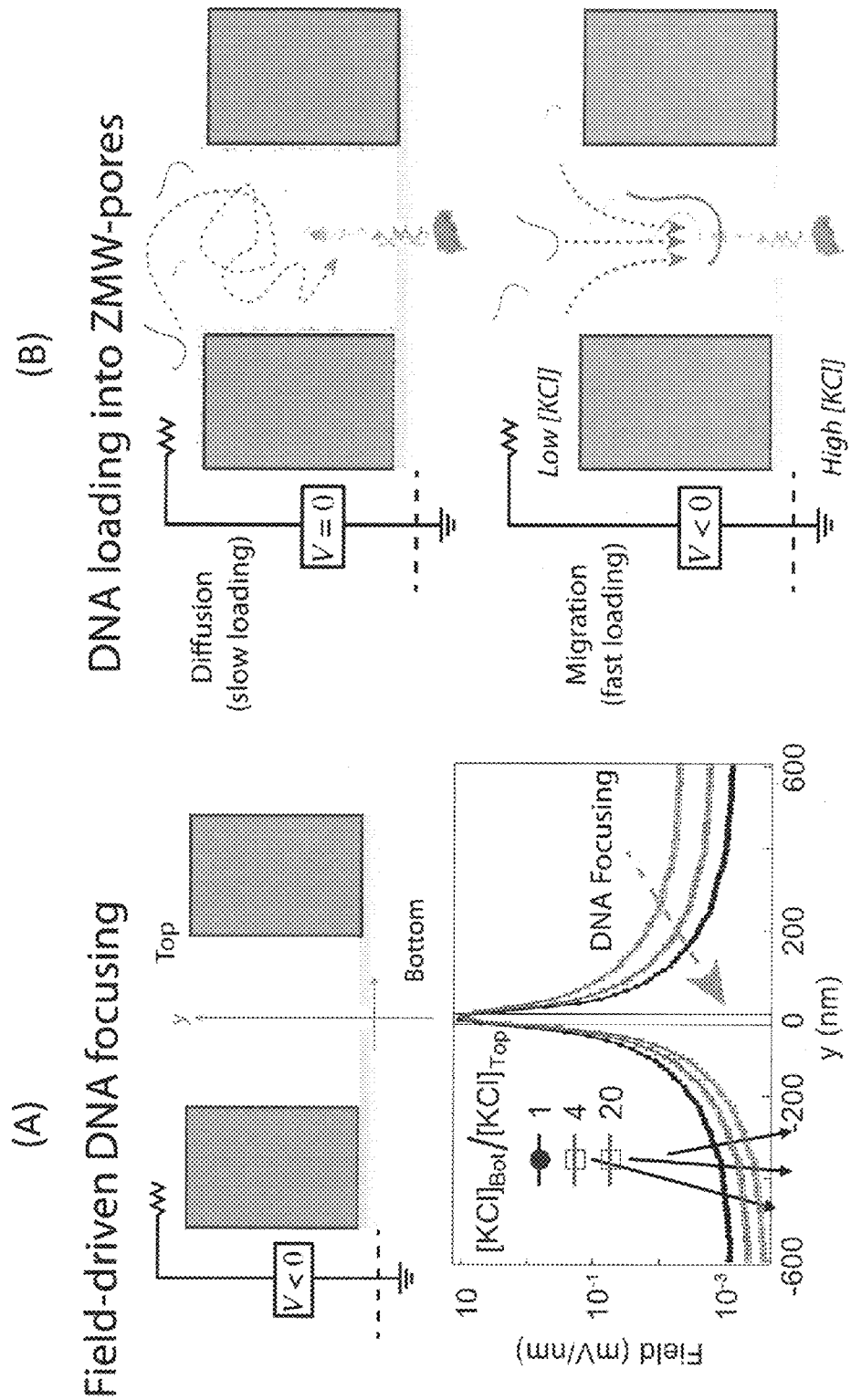
FIG. 4(A) illustrates field driven DNA focusing
FIG. 4(B) illustrates using field driven DNA focusing to load DNA into ZMWs.

FIG. 4 illustrates the reduction of input DNA required for SMRT sequencing by using ZMW-nanopore devices. FIG. 4(A) illustrates the principle of DNA focusing a pore with simulated electric field decay profiles for a 3.5 nm pore. When voltage and/or a salt gradient across the pore are applied, DNA is focused hundreds of nm away from the pore. FIG. 4(B) shows a scheme of free DNA diffusion vs. field-driven migration of DNA molecules towards a DNA polymerase molecule in a ZMW-nanopore device. The field-driven focusing can be used to load any suitable molecules into the ZMWs. For example, field-driven focusing can be used to load polymerase or polymerase-nucleic acid complex.

Figure 5:
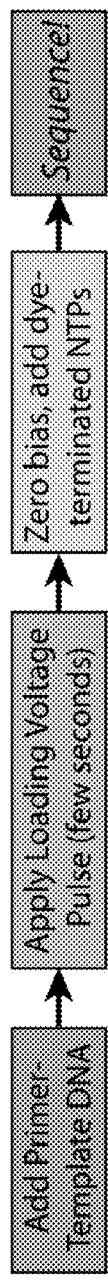
FIG. 5(A) shows an exemplary work flow of a method of the invention.
FIG. 5(B) illustrates carrying out real time single molecule sequencing on picogram level samples.
Figure 5:
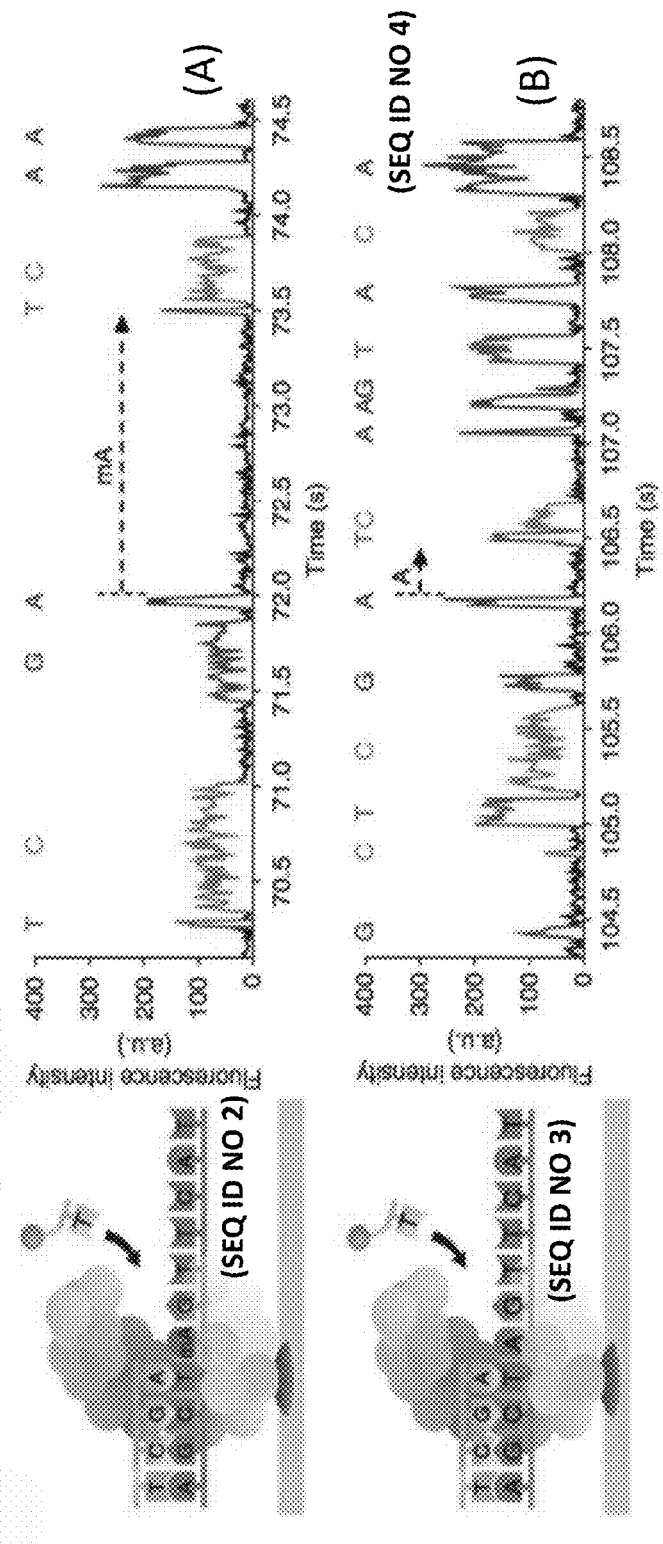

FIG. 5(A) shows a workflow for a method of the invention that integrates active DNA loading with SMRT sequencing to enable sequencing from picograms of DNA input. FIG. 5(B) illustrates how a method of the invention can provide for epigenetic sensitivity during single molecule real time sequencing. When N6-methyladenine (mA) is present in a bacterial DNA template, polymerase-catalyzed incorporation of the cognate thymine is significantly retarded as compared to a normal adenine (A), see Flusberg, B. A. et al. Nature Methods 2010, 7 (6), 461-465 incorporated in its entirety herein by reference, ZMW-nanopore devices should provide for the efficient loading of picogram levels of human brain mitochondrial DNA for epigenetic analysis.

The devices and methods of the invention provide for analysis of human mitochondrial. DNA (mtDNA) from brain samples of normal and diseased patients. For example, sequences can be compared with available data and epigenomic information and assessed based on the statistics of the incorporation kinetics to discriminate among various cytosine modifications and modified purines.

Nucleic Acid Templates

The template nucleic acid can be derived from any suitable natural or synthetic source. In preferred embodiments, the template comprises DNA, but in some circumstances double-stranded RNA or RNA-DNA heteroduplexes can be used. The template nucleic acid can be genomic DNA from eukaryotes, bacteria, or archaea. The template nucleic acid can be cDNA derived from any suitable source including messenger RNA. The template nucleic acid can comprise a library of double stranded segments of DNA. The template nucleic acid can be linear or circular. For example, the nucleic acid can be topologically circular and have a linear double stranded region. A circular nucleic acid can be, for example, a gapped plasmid. In some embodiments the nucleic acid is a double stranded linear DNA having a gap in one of the strands. The gap provides a site for attachment of the polymerase enzyme for nucleic acid synthesis. The linear double stranded DNA having a double-stranded DNA adaptor can be made by ligation of DNA fragment to an adaptor through blunt end-ligation or sticky end ligation. The ligation produces a linear DNA having a gap close to the 5' end of one or both of the strands. The gap can be any suitable width. For example, the gap can be from 1 to 50 bases, from 2 to 30 bases, or from 3 to 12 bases.

The terms "nucleic acid" or "oligonucleotide" or grammatical equivalents herein mean at least two nucleotides covalently linked together. A nucleic acid of the present invention will generally contain phosphodiester bonds, although in some cases, nucleic acid analogs are included that may have alternate backbones, comprising, for example, phosphoramide, phosphorothiate, phosphorodithioate, and peptide nucleic acid backbones and linkages. Other analog nucleic acids include those with positive backbones, non-ionic backbones, and non-ribose backbones, including those described in U.S. Pat. Nos. 5,235,033 and 5,034,506. The template nucleic acid may also have other modifications, such as the inclusion of heteroatoms, the attachment of labels, or substitution with functional groups which will still allow for base pairing and for recognition by the enzyme.

The template sequence may be provided in any of a number of different format types depending upon the desired application. The template may be provided as a circular or functionally circular construct that allows redundant processing of the same nucleic acid sequence by the synthesis complex. Use of such circular constructs has been described in, e.g., U.S. Pat. No. 7,315,019 and U.S. patent application Ser. No. 12/220,674, filed Jul. 25, 2008. Alternate functional circular constructs are also described in U.S. patent application Ser. No. 12/383,855, filed Mar. 27, 2009, and U.S. Pat. No. 8,153,375 Compositions and Methods for Nucleic Acid Sequencing; U.S. Pat. No. 8,003,330 Error-Free Amplification of DNA for Clonal Sequencing; and U.S. Ser. No. 13/363,066 filed Jan. 31, 2012 Methods and Compositions for Nucleic Acid Sample Preparation, the full disclosures of each of which are incorporated herein by reference in their entirety for all purposes.

Briefly, such alternate constructs include template sequences that possess a central double stranded portion that is linked at each end by an appropriate linking oligonucleotide, such as a hairpin loop segment. Such structures not only provide the ability to repeatedly replicate a single molecule (and thus sequence that molecule), but also provide for additional redundancy by replicating both the sense and antisense portions of the double stranded portion. In the context of sequencing applications, such redundant sequencing provides great advantages in terms of sequence accuracy.

The nucleic acids can comprise a population of nucleic acids having universal sequence regions that are common to all of the nucleic acids in the population and also have specific regions that are different in the different members of the population. The current invention allows for capturing and isolating polymerase-nucleic acid complexes using either the universal or the specific regions.

While in many cases nucleic acid synthesis is describe herein as extending from a primer, it is to be understood that some polymerases do not require an added external primer, and can be initiated using terminal protein. Polymerases that can be initiated using terminal protein include phi-29 polymerase.

Polymerase Enzymes

Polymerase enzymes useful in the invention include polymerases mutated to have desirable properties for sequencing. For example, suitable enzymes include those taught in, e.g., 61/593,569 filed Feb. 1, 2012 Recombinant Polymerases with Increased Phototolerance; US 20120034602 Recombinant Polymerases for Improved Single Molecule Sequencing; US 20100093555 Enzymes Resistant to Photodamage; US 20110189659 Generation of Modified Polymerases for Improved Accuracy in Single Molecule Sequencing; US 20100112645 Generation of Modified Polymerases for Improved Accuracy in Single Molecule Sequencing; US 2008/0108082 Polymerase enzymes and reagents for enhanced nucleic acid sequencing; US 20110059505 Polymerases for Nucleotide Analogue Incorporation; and U.S. Provisional Patent No. 61/708,469 filed Oct. 1, 2012, all of which are incorporated by reference herein for all purposes. The modified polymerases can have modified properties such as e.g., decreased branch fraction formation, improved specificity, improved processivity, altered rates, improved retention time, improved stability of the closed complex, etc.

In addition, the polymerases can be further modified for application-specific reasons, such as to increase photostability, e.g., as taught in U.S. patent application Ser. No. 12/384,110 filed Mar. 30, 2009, by Keith Bjornson et al. entitled "Enzymes Resistant to Photodamage," to improve activity of the enzyme when bound to a surface, as taught, e.g., in WO 2007/075987 ACTIVE SURFACE COUPLED POLYMERASES by Hanzel et al. and WO 2007/076057 PROTEIN ENGINEERING STRATEGIES TO OPTIMIZE ACTIVITY OF SURFACE ATTACHED PROTEIN S by Hanzel et al., or to include purification or handling tags as is taught in the cited references and as is common in the art. While the current method does not typically include light illumination, there is generally no issue with photostability. However, it will be understood that the electron transfer processes of electrochemistry can create reactive species analogous to reactive species formed during photonic excitation. Similarly, the modified polymerases described herein can be employed in combination with other strategies to improve polymerase performance, for example, reaction conditions for controlling polymerase rate constants such as taught in U.S. patent application Ser. No. 12/414,191 filed Mar. 30, 2009, and entitled "Two slow-step polymerase enzyme systems and methods," incorporated herein by reference in its entirety for all purposes.

The polymerase enzymes used in the invention will generally have strand-displacement activity. Many polymerases have this capability, and it is useful in the context of the current invention for opening up and exposing the regions of a nucleic acid sample for capture by a hook molecule. In some cases, strand displacement is part of the polymerase enzyme itself. In other cases, other cofactors or co-enzymes can be added to provide the strand displacement capability.

DNA Polymerases

DNA polymerases are sometimes classified into six main groups based upon various phylogenetic relationships, e.g., with *E. coli* Pol I (class A), *E. coli* Pol II (class B), *E. coli* Pol III (class C), Euryarchaeotic Pol II (class D), human Pol beta (class X), and *E. coli* UmuC/DinB and eukaryotic RAD30/xeroderma pigmentosum variant (class Y) which are incorporated by reference herein for all purposes. For a review of recent nomenclature, see, e.g., Burgers et al. (2001) "Eukaryotic DNA polymerases: proposal for a revised nomenclature" J Biol Chem. 276(47):43487-90. For a review of polymerases, see, e.g., Hübscher et al. (2002) "Eukaryotic DNA Polymerases" Annual Review of Biochemistry Vol. 71: 133-163; Alba (2001) "Protein Family Review: Replicative DNA Polymerases" Genome Biology 2(1): reviews 3002.1-3002.4; and Steitz (1999) "DNA polymerases: structural diversity and common mechanisms" J Biol Chem 274:17395-17398, which are incorporated by reference herein for all purposes. The basic mechanisms of action for many polymerases have been determined. The sequences of literally hundreds of polymerases are publicly available, and the crystal structures for many of these have been determined, or can be inferred based upon similarity to solved, crystal structures of homologous polymerases. For example, the crystal structure of Φ29, a preferred type of parental enzyme to be modified according to the invention, is available.

In addition to wild-type polymerases, chimeric polymerases made from a mosaic of different sources can be used. For example, Φ29 polymerases made by taking sequences from more than one parental polymerase into account can be used as a starting point for mutation to produce the polymerases of the invention. Chimeras can be produced, e.g., using consideration of similarity regions between the polymerases to define consensus sequences that are used in the chimera, or using gene shuffling technologies in which multiple Φ29-related polymerases are randomly or semi-randomly shuffled via available gene shuffling techniques (e.g., via "family gene shuffling"; see Crameri et al. (1998) "DNA shuffling of a family of genes from diverse species accelerates directed evolution" Nature 391:288-291; Clackson et al. (1991) "Making antibody fragments using phage display libraries" Nature 352:624-628; Gibbs et al. (2001) "Degenerate oligonucleotide gene shuffling (DOGS): a method for enhancing the frequency of recombination with family shuffling" Gene 271:13-20; and Hiraga and Arnold (2003) "General method for sequence-independent site-directed chimeragenesis: J. Mol. Biol. 330:287-296) which are incorporated by reference herein for all purposes. In these methods, the recombination points can be predetermined such that the gene fragments assemble in the correct order. However, the combinations, e.g., chimeras, can be formed at random. For example, using methods described in Clarkson et al., five gene chimeras, e.g., comprising segments of a Phi29 polymerase, a PZA polymerase, an M2 polymerase, a B103 polymerase, and a GA-1 polymerase, can be generated. Appropriate mutations to improve branching fraction, increase closed complex stability, or alter reaction rate constants can be introduced into the chimeras.

Available DNA polymerase enzymes have also been modified in any of a variety of ways, e.g., to reduce or eliminate exonuclease activities (many native DNA polymerases have a proof-reading exonuclease function that interferes with, e.g., sequencing applications), to simplify production by making protease digested enzyme fragments such as the Klenow fragment recombinant, etc. As noted, polymerases have also been modified to confer improvements in specificity, processivity, and improved retention time of labeled nucleotides in polymerase-DNA-nucleotide complexes (e.g., WO 2007/076057 POLYMERASES FOR NUCLEOTIDE ANALOGUE INCORPORATION by Hanzel et al. and WO 2008/051530 POLYMERASE ENZYMES AND REAGENTS FOR ENHANCED NUCLEIC ACID SEQUENCING by Rank et al.), to alter branch fraction and translocation (e.g., U.S. patent application Ser. No. 12/584,481 filed Sep. 4, 2009, by Pranav Patel et al. entitled "ENGINEERING POLYMERASES AND REACTION CONDITIONS FOR MODIFIED INCORPORATION PROPERTIES"), to increase photostability (e.g., U.S. patent application Ser. No. 12/384,110 filed Mar. 30, 2009, by Keith Bjornson et al. entitled "Enzymes Resistant to Photodamage"), and to improve surface-immobilized enzyme activities (e.g., WO 2007/075987 ACTIVE SURFACE COUPLED POLYMERASES by Hanzel et al. and WO 2007/076057 PROTEIN ENGINEERING STRATEGIES TO OPTIMIZE ACTIVITY OF SURFACE ATTACHED PROTEINS by Hanzel et al.) which are incorporated by reference herein for all purposes. Any of these available polymerases can be modified in accordance with the invention to decrease branching fraction formation, improve stability of the closed polymerase-DNA complex, and/or alter reaction rate constants.

Many such polymerases that are suitable for modification are available, e.g., for use in sequencing, labeling and amplification technologies. For example, human DNA Polymerase Beta is available from R&D systems. DNA polymerase I is available from Epicenter, GE Health Care, Invitrogen, New England Biolabs, Promega, Roche Applied Science, Sigma Aldrich and many others. The Klenow fragment of DNA Polymerase I is available in both recombinant and protease digested versions, from, e.g., Ambion, Chimerx, eEnzyme LLC, GE Health Care, Invitrogen, New England Biolabs, Promega, Roche Applied Science, Sigma Aldrich and many others. Φ29 DNA polymerase is available from e.g., Epicentre. Poly A polymerase, reverse transcriptase, Sequenase, SP6 DNA polymerase, T4 DNA polymerase, T7 DNA polymerase, and a variety of thermostable DNA polymerases (Taq, hot start, titanium Taq, etc.) are available from a variety of these and other sources. Recent commercial DNA polymerases include Phusion™ High-Fidelity DNA Polymerase, available from New England Biolabs; GoTaq® Flexi DNA Polymerase, available from Promega; RepliPHi™ Φ29 DNA Polymerase, available from Epicentre Biotechnologies; Pfu-Ultra™ Hotstart DNA Polymerase, available from Stratagene; KOD HiFi DNA Polymerase, available from Novagen; and many others. Biocompare(dot)com provides comparisons of many different commercially available polymerases.

DNA polymerases that are preferred substrates for mutation to decrease branching fraction, increase closed complex stability, or alter reaction rate constants include Taq polymerases, exonuclease deficient Taq polymerases, E. coli DNA Polymerase 1, Klenow fragment, reverse transcriptases, Φ29-related polymerases including wild type Φ29 polymerase and derivatives of such polymerases such as exonuclease deficient forms, T7 DNA polymerase, T5 DNA polymerase, an RB69 polymerase, etc.

In one aspect, the polymerase that is modified is a Φ29-type DNA polymerase. For example, the modified recombinant DNA polymerase can be homologous to a wild-type or exonuclease deficient Φ29 DNA polymerase, e.g., as described in U.S. Pat. Nos. 5,001,050, 5,198,543, or 5,576,204 which are incorporated by reference herein for all purposes. Alternately, the modified recombinant DNA polymerase can be homologous to other Φ29-type DNA polymerases, such as B103, GA-1, PZA, Φ15, BS32, M2Y, Nf, G1, Cp-1, PRD1, PZE, SF5, Cp-5, Cp-7, PR4, PR5, PR722, L17, Φ21, or the like. For nomenclature, see also, Meijer et al. (2001) "Φ29 Family of Phages" Microbiology and Molecular Biology Reviews, 65(2):261-287. Suitable polymerases are described, for example, in U.S. patent application Ser. No. 12/924,701, filed Sep. 30, 2010; and Ser. No. 12/384,112, filed Mar. 30, 2009 which is incorporated by reference herein for all purposes.

RNA Dependent RNA Polymerases

In some embodiments, the polymerase enzyme that is used for sequencing is an RNA polymerase. Any suitable RNA polymerase (RNAP) can be used including RNA polymerases from bacteria, eukaryotes, viruses, or archea. Suitable RNA polymerases include RNA Pol I, RNA Pol II, RNA Pol II, RNA Pol IV, RNA Pol V, T7 RNA polymerase, T3 RNA polymerase or SP6 RNA polymerase. The use of RNA polymerases allows for the direct sequencing of messenger RNA, transfer RNA, non-coding RNA, ribosomal RNA, micro RNA or catalytic RNA. Where RNA polymerases are used, the polymerizing reagents will generally include NTPs or their analogs rather than the dNTPs used for DNA synthesis. In addition, RNA polymerases can be used with specific cofactors. There are many proteins that can bind to RNAP and modify its behavior. For instance, GreA and GreB from E. coli and in most other prokaryotes can enhance the ability of RNAP to cleave the RNA template near the growing end of the chain. This cleavage can rescue a stalled polymerase molecule, and is likely involved in proofreading the occasional mistakes made by RNAP. A separate cofactor, Mfd, is involved in transcription-coupled repair, the process in which RNAP recognizes damaged bases in the DNA template and recruits enzymes to restore the DNA. Other cofactors are known to play regulatory roles; i.e., they help RNAP choose whether or not to express certain genes. RNA dependent RNA polymerases (RNA replicases) may also be used including viral RNA polymerases: e.g. polioviral 3Dpol, vesicular stomatitis virus L, and hepatitis C virus NS5b protein; and eukaryotic RNA replicases which are known to amplify microRNAs and small temporal RNAs and produce double-stranded RNA using small interfering RNAs as primers.

Reverse Transcriptases

The polymerase enzyme used in the methods or compositions of the invention includes RNA dependent DNA polymerases or reverse transcriptases. Suitable reverse transcriptase enzymes include HIV-1, M-MLV, AMV, and Telomere Reverse Transcriptase. Reverse transcriptases also allow for the direct sequencing of RNA substrates such as messenger RNA, transfer RNA, non-coding RNA, ribosomal KNA, micro RNA or catalytic RNA.

Thus, any suitable polymerase enzyme can be used in the systems and methods of the invention. Suitable polymerases include DNA dependent DNA polymerases, DNA dependent RNA polymerases, RNA dependent DNA polymerases (reverse transcriptases), and RNA dependent RNA polymerases.

Conditions for Nucleic Acid Synthesis

The conditions required for nucleic acid synthesis are well known in the art. The polymerase reaction conditions include the type and concentration of buffer, the pH of the reaction, the temperature, the type and concentration of salts, the presence of particular additives that influence the kinetics of the enzyme, and the type, concentration, and relative amounts of various cofactors, including metal cofactors. One aspect of carrying out sequencing chemistry is controlling the ionic strength of the medium. It is know that polymerase enzymes can effectively operate over a range of ionic strengths, and that the ionic strength can be varied by changing the levels of monovalent ions such as Li+, Na+, K+, Rb+, or Cs+. As has been shown the amount of one or more of these cations can have an effect on the kinetics of the polymerase, and that the kinetic behavior can be tuned by varying the relative amounts of these ions. Using combinations of these ions, conditions can be chosen where both the kinetic parameters of the enzyme, and the ionic strength for detection can be useful for the instant methods. See, e.g. U.S. Patent Application 20120009567 which is incorporated herein by reference for all purposes.

Enzymatic reactions are often run in the presence of a buffer, which is used, in part, to control the pH of the reaction mixture. Buffers suitable for the invention include, for example, TAPS (3-{[tris(hydroxymethyl)methyl]amino}propanesulfonic acid), Bicine (N,N-bis(2-hydroxyethyl)glycine), TRIS (tris(hydroxymethyl)methylamine), ACES (N-(2-Acetamido)-2-aminoethanesulfonic acid), Tricine (N-tris(hydroxymethyl)methylglycine), HEPES 4-2-hydroxyethyl-1-piperazineethanesulfonic acid), TES (2-{[tris(hydroxymethyl)methyl]amino}ethanesulfonic acid), MOPS (3-(N-morpholino)propanesulfonic acid), PIPES (piperazine-N,N'-bis(2-ethanesulfonic acid)), and MES (2-(N-morpholino)ethanesulfonic acid).

The pH of the reaction can influence the rate of the polymerase reaction. The temperature of the reaction can be adjusted to enhance the performance of the system. The reaction temperature may depend upon the type of polymerase which is employed.

Monitoring Biological Reactions

While ZMW with nanopore devices, systems, and methods of the invention are described throughout most of this application for use in nucleic acid sequencing, it is to be understood that these can also find use in other analytical reactions including monitoring biological reactions in real time, in particular monitoring the interactions of biological molecules at the single molecule level. The ability to analyze such reactions provides an opportunity to study those reactions as well as to potentially identify factors and/or approaches for impacting such reactions, e.g., to stimulate, enhance, or inhibit such reactions. For example, the methods of the invention can be used to obtain a single binding partner in each ZMW for use in measuring binding interactions.

The invention provides for observation of the interaction of two or more specifically interacting reactants at the single molecule (or single molecular complex) level in order to monitor the progress of the interaction separately from other interactions. In other words, a single immobilized reaction component can be monitored at a single reaction site on a support such that signals received from that reaction site are resolvable from other immobilized reaction components at other reaction sites on that support. A plurality of analytical reactions may also be carried out in an array of devices. Analytical reactions in an array of devices can be carried out simultaneously, and may or may not be synchronized with one another. In such an array, multiple reactions can therefore be monitored simultaneously and independently.

Reactant characteristic(s) and interaction characteristic(s) can be measured. Reactant characteristic(s) includes characteristics of a particular reactant, e.g., type/identity of reactant, concentration of the reactant, a label on the reactant, etc. Interaction characteristic(s) includes characteristics of a given interaction between multiple reactants, e.g., rates, constants, affinities, etc., and is typically determined based on reaction data gathered during such an interaction. For example, some characteristics of a polymerization reaction include the identity of a monomer incorporated into a growing polymer, the rate of incorporation, length of time the polymerase is associated with the template, and the length of the polymer synthesized. In some embodiments, various different components of an analytical reaction (e.g., different types of monomers) are differentially labeled to allow each labeled component to be distinguished from other labeled components during the course of the reaction. For example, incorporation of monomer A into a polymer can be distinguished from incorporation of monomer B.

In certain preferred embodiments, multiple characteristics of a reaction are monitored and/or determined. For example, these may be multiple characteristics of one or more reaction components (e.g., identity, concentration, etc.; "reactant characteristic(s)"), one or more characteristics of an interaction between two or more reaction components (e.g., related to product formation, kinetics of the reaction, binding or dissociation constants, etc.; "interaction characteristic(s)"), or, preferably, a combination reactant characteristic(s) and interaction characteristic(s).

In some embodiments, a reaction mixture comprises a plurality of types of non-immobilized binding partners, and a characteristic determined is the particular type of one of the non-immobilized binding partners, e.g., that associates with a particular reaction site. Typically, the label is attached to the non-immobilized through a linking group as described herein. In some embodiments, an array of reaction sites comprises a plurality of types of immobilized binding partners, each at a different reaction site, and a characteristic is determined that identifies which type of immobilized binding partner is located at each of the different reaction sites. In some embodiments, an array of reaction sites comprising a plurality of types of immobilized binding partners, each at a different reaction site, is contacted with a reaction mixture comprising a plurality of types of non-immobilized binding partners; characteristics determined during the reaction serve to both identify which of the types of immobilized binding partners is located at each reaction site and which of the types of non-immobilized binding partners associate with the immobilized binding partners. In some cases, the specificity of the interaction between the non-immobilized and immobilized binding partners is high enough that detection of a label on a non-immobilized binding partner residing at a particular reaction site is sufficient to identify the immobilized binding partner at that reaction site. In some embodiments, a characteristic is determined that quantifies a particular aspect of an interaction between reaction components, e.g., affinity between an immobilized binding partner and a non-immobilized binding partner, a rate of catalysis of a reaction, or other aspects of the interaction. For example, a non-immobilized binding partner can have a label that not only identifies it from a plurality of different non-immobilized binding partners, but also provides kinetic information about the reaction based on various parameters monitored in real time, e.g., the time it takes for binding to occur, the time it remains associated with the reaction, site, the on/off rate, etc.

In some embodiments, multiple different interactions or reactions can occur and be monitored simultaneously or sequentially, where each individual interaction is monitored separately from every other, such that there is resolution between different interactions under observation. For example, multiple different non-immobilized reaction components may simultaneously or sequentially interact with an immobilized reaction component; e.g., the multiple different non-immobilized reaction components can be different non-immobilized binding partners for an immobilized binding partner, or different agents that may alter an interaction between two reaction components, or different monomers for incorporation into a polymer being synthesized at the reaction site. In other embodiments, an interaction between a non-immobilized reaction component and a product of a synthesis reaction occurs during the synthesis reaction, e.g., once the product is suitable for such interaction. For example, the product may need to be of a certain length, or in a certain conformation (e.g., in a particular higher-order structure) to be suitable for interaction with the non-immobilized reaction component. Alternatively, a synthesis reaction can be performed at a reaction site, and subsequently exposed to a reaction mixture comprising non-immobilized reaction components that can then interact with the product of the synthesis reaction, which is preferably immobilized at the reaction site. In preferred embodiments, the synthesis reaction is monitored to determine characteristics of the product (e.g., length, chemical composition, etc.) being synthesized. Knowledge of characteristics of the product of synthesis combined with the detection of an interaction with a particular reaction component provides additional characteristics, e.g., the binding site for the particular reaction component. Examples of biological interactions that can be measured with the devices and systems of the invention are described, for example, in U.S. 20100323912 Patent Application Real-Time Analytical Methods and Systems which is incorporated herein by reference for all purposes.

Other Arrays of Single Polymerases

While the invention is described with respect to nanopores within ZMWs for single polymerase loading, the devices, methods, and systems of the invention can also be used to produce arrays of single polymerases that are not in ZMWs. For example, an array of nanopores can be produces wherein each nanopore is proximate to redox electrodes that are used for the detection of single molecules by electrochemistry. See, for example, U.S. patent application Ser. No. 13/989,478, filed Oct. 15, 2012, entitled Real-Time Redox Sequencing, which is incorporated by reference herein in its entirety for all purposes.

For example, a nanopore loading method as describe herein can be used to provide a single polymerase enzyme proximate to either a one-electrode or two-electrode redox sequencing configuration. The redox electrodes are produced near a thin region of the substrate, which allows for the production of a nanopore within nanometers of the electrode for enhancing the level of single molecule loading in the appropriate region.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually and separately indicated to be incorporated by reference for all purposes.

What is claimed is:

1. An array of zero mode waveguides, each zero mode waveguide comprising an aperture having walls and a base, the base comprising a thin membrane, the array comprising a top solution above the zero mode waveguides extending into each zero mode waveguide, and a bottom solution below the thin membranes comprising the bases of the zero mode waveguides, wherein each zero mode waveguide further comprises a nanopore extending through the thin membrane to the solution below the zero mode waveguide.

2. The array of claim 1 wherein each aperture extends through an opaque cladding layer to a base layer comprising the thin membrane.

3. The array of claim 2 wherein the opaque cladding layer comprises a metal.

4. The array of claim 2 wherein the opaque cladding layer comprises aluminum.

5. The array of claim 2 wherein the thin membrane comprises silicon nitride.

6. The array of claim 1 wherein the apertures have a cross sectional dimension of between about 20 nm and 300 nm.

7. The array of claim 1 wherein the nanopores have a cross sectional dimension between about 2 nm and 10 nm.

8. The array of claim 1 wherein the thin membrane has a thickness from 5 nm to 30 nm.

9. A method for isolating a single biomolecule within a zero mode waveguide comprising: providing an array of claim 1; exposing the bottom of the zero mode waveguide to the bottom solution, wherein the bottom solution comprises attachment molecules, the attachment molecules having a threading portion which can extend through the nanopore, and a blocking portion which does not pass through the nanopore, wherein the threading portion comprises a binding moiety; providing an electric field across the array that drives the threading portion of a single attachment molecule into the nanopore of a plurality of zero mode waveguides; adding biomolecules to the top solution, the biomolecules comprising a group capable of reaction with the binding moiety on an attachment molecule; allowing the biomolecules to react with the binding moiety whereby a single biomolecule is isolated within a single zero mode waveguide of a plurality of the zero mode waveguides.

10. The method of claim 9 wherein the blocking portions of the attachment molecules comprise a protein, a bead, or a nanoparticle.

11. The method of claim 9 wherein the biomolecule is connected to an avidin or a streptavidin.

12. The method of claim 9 wherein threading portion of the attachment molecules comprise a nucleic acid.

13. The method of claim 12 wherein the nucleic acid comprises a DNA.

14. The method of claim 9 wherein the binding moiety on the threading portion comprises a biotin.

15. The method of claim 9 wherein the group on the biomolecule capable of reacting with the binding moiety comprises an avidin or a streptavidin.

16. The method of claim 9 wherein the biomolecule comprises a polymerase enzyme.

17. A method for isolating single polymerase enzymes within a zero mode waveguides comprising: providing an array of claim 1; exposing the bottom of the zero mode waveguide to the bottom solution, wherein the bottom solution comprises attachment molecules, the attachment molecules having a threading portion which can extend through the nanopore, and a blocking portion which does not pass through the nanopore, wherein the threading portion comprises a binding moiety; providing an electric field across the array that drives the threading portion of a single attachment molecule into the nanopore of a plurality of zero mode waveguides; adding polymerase enzymes, each comprising a group capable of reaction with the binding moiety to the top solution; and allowing the polymerase enzymes to react with the binding moiety whereby a single polymerases enzyme is isolated in a single zero mode waveguide of a plurality of the zero mode waveguides.

18. The method of claim 17 further comprising adding nucleic acid templates to the top solution and providing an electric field across the array to drive the nucleic acid templates into the zero mode waveguides.

* * * * *